Figure 1:
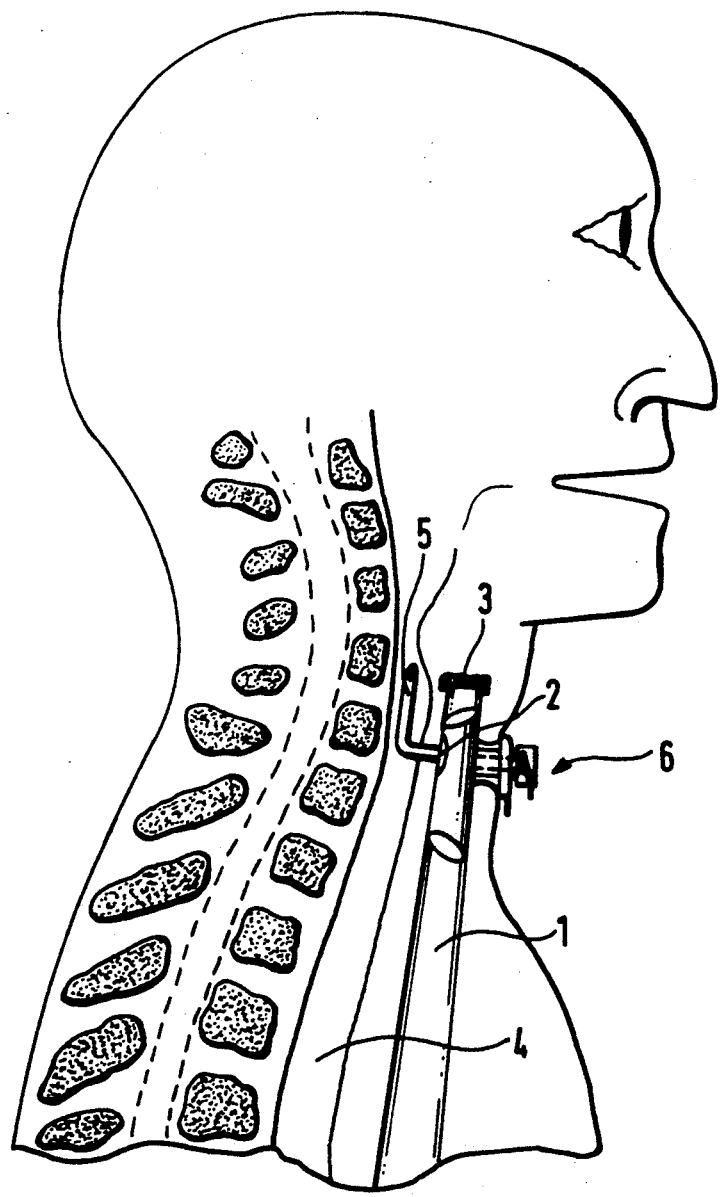

United States Patent [19]

Koss et al.

[11] Patent Number: 5,107,828
[45] Date of Patent: Apr. 28, 1992

[54] TRACHEOSTOMA CLOSURE DEVICE

[75] Inventors: Walter Koss, Industriestrasse, DE-6222 Geisenheim; Ingo F. Herrmann, Würzburg, both of Fed. Rep. of Germany

[73] Assignee: Walter Koss, Geisenheim, Fed. Rep. of Germany

[21] Appl. No.: 539,303

[22] Filed: Jun. 15, 1990

Related U.S. Application Data

[63] Continuation of Ser. No. 15,090, filed as PCT/EP86/00274, May 10, 1986, abandoned.

[51] Int. Cl.5 ............................................. A61M 16/00
[52] U.S. Cl. ........................... 128/200.26; 128/207.14; 128/207.16
[58] Field of Search ................ 128/207.14, 207.15, 128/207.16, 200.26; 137/512; 604/8; 623/9

[56] References Cited

U.S. PATENT DOCUMENTS

| | | | |
|---|---|---|---|
| 3,042,021 | 7/1962 | Read | 604/8 |
| 3,137,299 | 6/1964 | Tabor | 128/207.16 |
| 3,538,918 | 11/1970 | Engelsher | 128/200.26 |
| 3,605,751 | 9/1971 | Gulling | 128/207.14 |
| 3,721,233 | 3/1973 | Montgomery et al. | 128/207.14 |
| 3,952,335 | 4/1976 | Sorce et al. | 128/207.16 |
| 3,974,854 | 8/1976 | Kurpanek | 137/512 |
| 4,040,428 | 8/1977 | Clifford | 128/207.16 |
| 4,596,248 | 6/1986 | Lieberman | 128/207.16 |
| 4,627,433 | 12/1986 | Lieberman | 128/207.16 |

FOREIGN PATENT DOCUMENTS 0078685 5/1983 European Pat. Off. .
0132957 2/1985 European Pat. Off. .

Primary Examiner—Edgar S. Burr
Assistant Examiner—Aaron J. Lewis
Attorney, Agent, or Firm—Gifford, Groh, Sprinkle, Patmore and Anderson

[57] ABSTRACT

Described is a tracheostoma closure device which has a valve (18, 23) which can be actuated at will be breathing out, to permit the patient to speak. The arrangement has an open tube portion (10) which can be introduced into the stoma and from which extends a passage stump portion (7) which leads outwardly through the stoma and which on its front side carries a housing (9) for the valve. An adjustable flange ring (8) for sealing off the stoma is carried on the passage stump portion (7). The valve is formed by a non-return valve flap (18) which is mounted pivotally in the valve housing (9) and which opens in the direction of breathing in and closes in the direction of breathing out when a predetermined flow speed is exceeded.

28 Claims, 3 Drawing Sheets

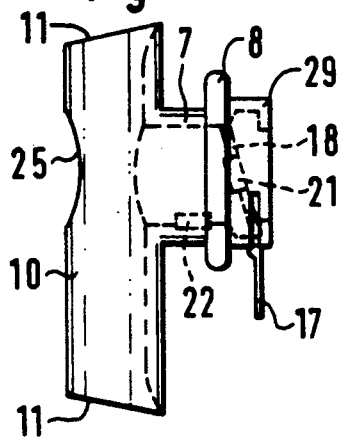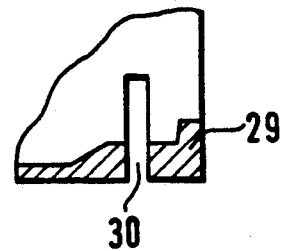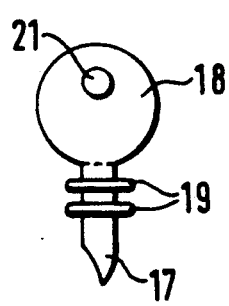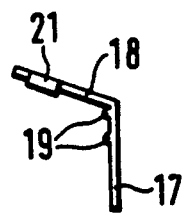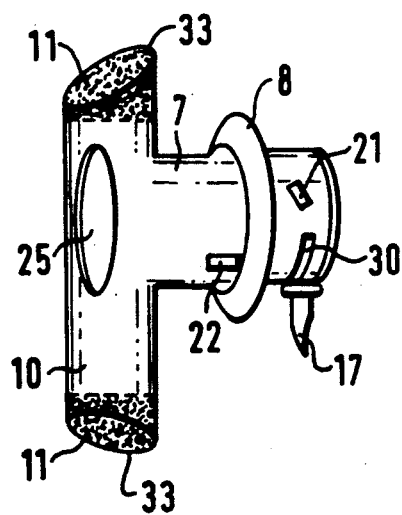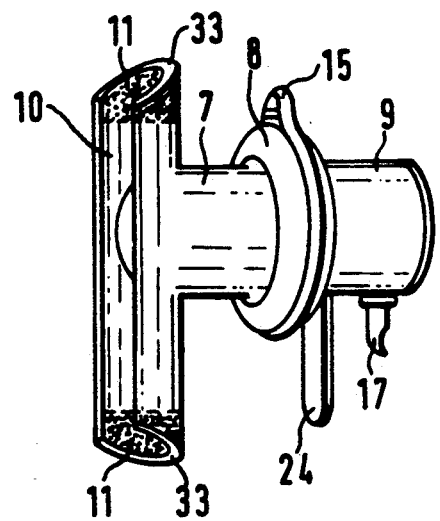

TRACHEOSTOMA CLOSURE DEVICE

This is a continuation of copending application Ser. No 07/015,090 filed as PCT/EP86/00274, May 10, 1986, now abandoned.

The present invention relates to a tracheostoma closure device as set forth in the classifying portion of claim 1. Such a closure device is disclosed in German utility model No 83 29 888 and corresponding German laid-open application (DE-OS) No 34 36 777.

Patients with a tracheostoma, that is to say an artificial opening in the neck region leading into the respiratory duct or trachea can speak after total operation in respect of the larynx in known manner by means of a speech or voice prosthesis which is operatively inserted as a communication between the respiratory duct and the esophagus. For the purposes of speech however the tracheostoma then has to be closed. For that purpose, the patients usually make use of a finger which is applied to the opening and which prevents the air from flowing out at that location. In order to simplify speaking, it is already known for a diaphragm valve to be mounted on the opening, more specifically using an adhesive film or foil. However that arrangement suffers from difficulties in regard to durability and a sealing effect. Furthermore such valves are sensitive to fouling or contamination, in regard to proper functioning thereof.

The tracheostoma closure device disclosed in the above-mentioned specifications represents a tried and tested solution to the above-discussed problems It is such that it can be easily and securely fitted in position and can be conveniently handled by the patient. However, movements therein are desired.

Accordingly, the present invention is based on the object of so developing the known tracheostoma closure device as to permit a higher rate of air flow therethrough with a smaller structural height and to provide a further improvement in mounting and handling thereof. The device which attains that object is set forth in claim 1. The valve flap provides a large through-flow cross-section with a good and reproducible response sensitivity.

Many further developments are also possible. Thus the valve flap and/or the seat thereof may comprise a flexible or yielding material in such a way that, after closing, the flap can pass through its seat if the predetermined dynamic pressure is exceeded. That particular design configuration provides the necessary safety aspect for a sudden discharge of breath, for example when coughing, must always remain possible. When the valve flap has passed through its seat, it can be pressed back into its normal position again by hand, without removing the closure device.

The safety feature may also be embodied in per se known manner however in that the valve housing is fitted onto the tubular or passage stump portion and then if necessary can be pulled off or removed by coughing.

The valve flap may be mounted in the region of the valve housing which is the lower region in the operative position of the device, and can be held in the opened position by an additional weight. The valve flap only performs its non-return function when a given flow speed is exceeded when breathing, that is to say the patient wants to close the valve flap at will in order to speak by an abrupt discharge of breath. To avoid the point of closure being dependent on position, for example when stooping over, the valve flap may have a magnet which co-operates with a further magnet on or in the wall of the valve housing and which holds the valve flap in the opened condition. The term magnet in that respect is intended to mean that at least one component of the respective co-operating pair is a permanent magnet. The other component may comprise soft-magnetic material, for example a small iron plate. Another possible way of holding the valve flap in the opened condition until a given speed of discharge flow is attained provides that the flap is urged into the opened position by a spring force. The spring force may be applied by the mounting means of the flap itself, for example in the form of a film hinge, or also by means of a separate spring.

For the purposes of adaptation to the respective patients and their living and speaking habits, it is advantageous if the force with which the valve flap is held in the open condition is easily adjustable. For that purpose a development of the invention provides that the mounting location of the valve flap is displaceable in the peripheral direction of the tubular passage stump portion. In the case of an additional weight, the effective component due to the force of gravity can then be varied and when using a magnet the displacement of the mounting location alters the magnetic force by virtue of an alteration in the mutually oppositely disposed effective surfaces of the magnets. However there is also the possibility of making the spacing of the magnets in the opened condition of the valve flap adjustable, for example by means of a stop screw, in order to adjust the level of response sensitivity.

In order to provide for the above-mentioned displacement in the peripheral direction, it may be provided that the valve housing is fitted onto the passage stump portion and is rotatable with respect thereto. So that the force applied to the passage portion and therewith the stoma and the trachea is kept at a low level, when the valve housing is rotated with respect to the passage portion in order to adjust the level of response sensitivity, it may be provided that in the region of its contact surface with the valve housing, the passage portion has a peripherally extending bead or flange portion thereon. The valve housing then slides with its inside edge on the narrow bead or flange portion, instead of on the entire contact surface. So that the valve housing cannot fall off too easily, a peripherally extending bead or flange portion may also be provided in the region of its contact surface with the passage portion, the further bead or flange portion on the valve housing snapping behind the bead or flange portion on the passage portion when the valve housing is pressed onto the passage portion. One of the peripherally extending bead or flange portions may also have interruptions therein without adversely affecting the sealing action produced.

In a further development of the invention however the valve housing may also be an integral part of the passage portion. In that arrangement but also when the valve housing is a separate component, the valve flap may advantageously be in the form of a thin plate or disc which is connected by way of a film hinge to a radial extension portion which is fitted sealingly through a slot in the wall of the valve housing and which preferably has an abutment means which defines and delimits the depth of engagement therein. In order to provide adjustability in respect of the air speed necessary for closure of the device, with a one-piece construction of the passage stump portion and the valve housing, the slot may be of such a width in the peripheral direction of the valve housing that the extension portion of the valve housing is displaceable in respect of its angular position.

In some cases it has been found that a depression or inwardly extending area occurs in the lower region of the tracheostoma, and that makes it difficult to provide a seal. For that purpose, a further development of the invention provides that the displaceable flange ring which is in contact with the tracheostoma in that region has a recess or cut-away portion over a part of its periphery. In addition or instead thereof, the flange ring may also be made from material of a different degree of hardness in such a way that in the region of the depression at the tracheostoma the ring is of a soft material which bears closely thereagainst. Furthermore, individual adaptation of the shape of the flange ring to the anatomical situation is also possible. Furthermore, the flange ring may be provided with a radially projecting bar portion which has a bore therein and which makes it possible to fit a tape leading to the removable valve housing. The valve housing is then prevented from becoming lost. Instead of that, the valve housing may also be fixed by means of a tape to a radially projecting bar portion on the passage stump portion. The flange rings may then be of a symmetrical configuration so that they are easier to handle by the patient.

In the known tracheostoma closure device discussed in the opening part of this specification the terminal sealing member comprises a flange. A further development of the invention provides that the terminal sealing member is a tube portion which is fitted to the inward end of the passage stump portion and which is open with respect thereto. That assumes that the trachea is not guided in a bent configuration to the stoma in the otherwise conventional manner, but that, after removal of the larynx, the trachea has a cover fitted thereon and the stoma is formed in the side of the trachea. That also provides a stoma of large size and volume with a correspondingly large cross-section for the closure device.

The ends of the tube portion are desirably angled in such a way that the tube portion is shorter at the side thereof which is in opposite relationship to the passage stump portion. For the purposes of fitting a voice prosthesis into the tracheostoma closure device, the tube portion advantageously has an opening at the wall thereof which is in opposite relationship to the passage stump portion.

The voice prosthesis can then be introduced into the esophagus through the above-mentioned opening and the wall of the trachea. Another possibility would be for the tube portion to be completely opened at the side in opposite relationship to the passage stump portion, thus giving a channel-like structure instead of the tubular structure.

The tracheostoma closure device according to the invention is desirably made from an elastomer plastic material, preferably silicone rubber. In that arrangement, the tubular portion is produced from a material which is made soft, to avoid irritation, in the region of the ends thereof. The sealing disc with its radial extension portion and the film hinge may also be made from a resilient plastic material, in particular a polyacetate resin (POM).

Figure 2:
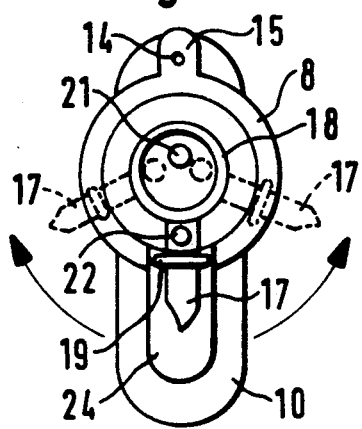
Figure 3:
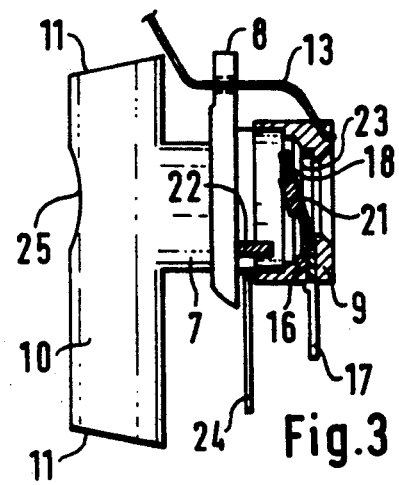
Figure 4:
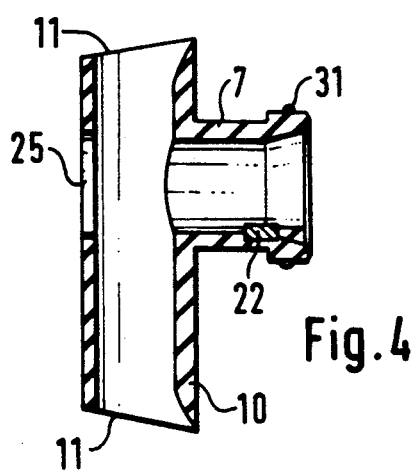
Figure 5:
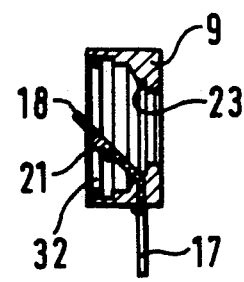

The invention will be described hereinafter by means of embodiments with reference to the accompanying drawings in which:

FIG. 1 is a diagrammatic sectional view of the neck and head region of a patient with a tracheostoma into which is fitted a valve closure device in accordance with one embodiment of the invention, FIG. 2 shows a front view of an assembled closure device according to the invention, FIG. 3 is a partly sectional side view of the closure device shown in FIG. 2, FIG. 4 is a sectional side view of the closure device shown in FIGS. 2 and 3 with the flange ring and the valve body removed, FIG. 5 is a sectional side view of the valve body with valve flap fitted therein for the closure device shown in FIGS. 2 through 4, FIG. 6 is a view on an enlarged scale of the valve flap for the closure device shown in FIGS. 2 through 5, FIG. 7 is a view of the flange ring for the closure device shown in FIGS. 2 through 5, FIG. 8 shows a modified flange ring for the closure device shown in FIGS. 2 through 5, FIG. 9 is a side view of a further embodiment of a closure device according to the invention, FIG. 10 is a view on an enlarged scale showing a portion of the closure device of FIG. 9 in the region of the valve body, FIG. 11 is a front view on an enlarged scale of the valve flap for the closure device shown in FIGS. 9 and 10, FIG. 12 is a side view on an enlarged scale of the valve flap shown in FIG. 11, in the bent-over condition, FIG. 13 is a perspective view of the closure device shown in FIGS. 9 and 10, and FIG. 14 is a perspective view of the closure device shown in FIGS. 2 through 5, with modified terminal sealing member.

FIG. 1 diagrammatically shows the way in which a tracheostoma closure device according to the invention is arranged. After total operation in respect of the larynx the respiratory duct (trachea) 1 communicates with the outside air by way of a front opening which is cut using a stencil or template, and a stoma 2. A cover 3 of muscle tissue closes off the trachea at the cut end thereof. What is referred to as a speech or voice prosthesis 5 leads into the esophagus 4 through a communication which is produced by operation between the trachea 1 and the esophagus 4. The prosthesis 5 permits speech even without the larynx and such prostheses are known. So that now the patient can speak by breathing out air by way of the speech prosthesis 5, the stoma 2 must be closed. That is affected either by applying a finger or by means of a valve closure device 6. Embodiments of valve closure devices 6 in accordance with the invention are described in greater detail hereinafter.

In the embodiment illustrated in FIGS. 2 through 7, the device has a tubular or passage stump portion 7 with a flange ring 8 fitted thereon, and a cup-like valve housing 9. A tubular portion 10 with angled end surfaces 11 is joined to the rearward (proximal) end of the passage stump portion 7. As shown in FIG. 1, the tubular portion 10 is later disposed in the trachea 1 and the passage portion 7 leads to the exterior through the stoma 2. As the closure device is overall made from soft-elastic material, for example silicone rubber, of a quality which is permitted for medical purposes, the tube portion 10 can also be subsequently inserted into the trachea 1 through the stoma 2. It is also possible however for the closure device to be introduced during the operation as a means for keeping the place available. The displaceable flange ring 8 is pressed sealingly against the skin of the patient. In that respect, the lower region of the flange ring 8 may be provided with a recess or cut-away portion 12 (see FIG. 8) which permits better adaptation to the anatomical situation in the lower region of the stoma 2.

The rotatable valve housing 9 which is fitted onto the passage stump portion 7 is connected to the flange ring 8 by way of a tape or strip 13 which goes to a bore 14 (see FIGS. 7 and 8) in a radial lug 15, so that the valve housing 9 cannot become lost even after having been removed from the passage stump portion 7. Instead of that, the tape or strip 13 may also be connected to a radial extension portion 24 on the passage stump portion 7 (that arrangement is not shown) so that the flange ring 8 remains free and can be easily replaced. If the flange ring 8 is symmetrically rounded off on both sides (see FIG. 9), it can be fitted as desired onto the passage stump portion 7 in both directions. The valve housing 9 is made easier to rotate on the passage stump portion 7, by means of the provision of a peripherally extending bead or flange portion 31 in the front region of the passage stump portion 7. The valve housing 9 then essentially slides on the bead portion 31. A corresponding bead or flange portion 32 on the inside of the valve housing 9 snaps over the bead portion 31 after the valve housing has been fitted into position, and prevents it from accidentally falling off.

Figure 6:
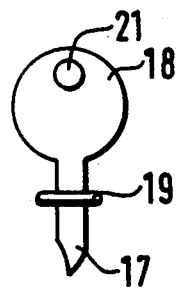
Figure 7:
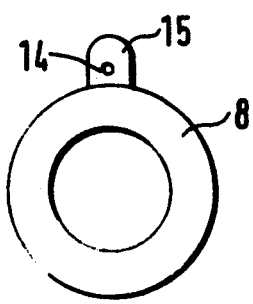
Figure 8:
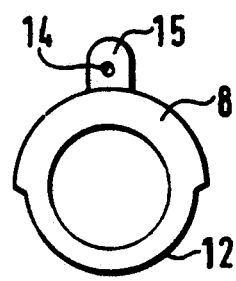

In the front lower region the valve housing 9 has a slot 16 through which passes the radial extension portion 17 of a valve flap 18 which is in the form of a disc (see also FIG. 6). The radial extension portion 17 has an abutment or stop means in the form of a web 19 which is pulled through the slot 16 until it just comes out and bears against the lower wall of the valve housing 9. The valve flap 18 is then in the proper position in the valve housing 9. The "hinge" of the valve flap 18 is what is referred to as a film hinge, in the form of a portion 20 of reduced thickness of material, at the transition from the extension portion 17 to the disc-like valve flap 18.

In its upper region the valve flap 18 carries a small flat magnetic 21 which is disposed for example in a thin-skinned pocket (not shown) and covered with plastic material. A further magnet 22 (see FIG. 4) is embedded into the inside wall of the passage stump portion 7. When the valve housing 9 is in the angular position shown in solid lines in FIG. 2 and the valve flap is urged downwardly when the patient breathes in, a magnetic attraction force occurs between the two magnets 21 and 22. In that respect only one of the two magnets needs to be a permanent magnet. The respective other member may comprise a simple iron member with suitable corrosion protection therefor. The magnetic attraction force between the magnets 21 and 22 is such that it is only at a comparatively high flow speed when the patient breathes out that the flap 18 is moved so that its magnet 21 lifts away from the magnet 22 and the flap lies sealingly against its seat 23, thus performing its non-return or check valve function. The patient can produce that closing movement of the valve at will, by briefly breathing out in the form of a pant. After the flap 18 is closed the patient can then speak using the voice prosthesis 5.

In order to adjust the magnetic holding force as between the magnets 21 and 22, the valve housing 9 may be turned in both directions, preferably by using a handle or gripping portion 24, over an angular range of for example 50° at each side, as indicated in FIG. 2. The two magnets 21 and 22 then no longer lie against each other over the entire surface thereof, in the open condition of the valve flap 18, so that the holding force is reduced. The discharge flow speed at which the flap 18 closes is correspondingly reduced.

As it is always necessary to ensure that the valve opens in the event of the patient breathing out vigorously, for example when coughing, the valve flap 18 is made from a soft-elastic material and is of such a dimension that, when a certain dynamic pressure occurs, the valve flap 18 surmounts its seat 23 and passes out of the valve housing 9 in a forward direction. Instead of that however the valve housing 9 may also be of such a configuration that it is automatically pushed off when the patient coughs.

Instead of the magnetic holding force between the magnets 21 and 22, the valve flap 18 may also be provided only with an additional weight which is for example similar in shape to the magnet 21. The weight and the hinge configuration must then be such that in the rest condition, that is to say, without any air flowing through the valve, the flap 18 bears against the bottom of the passage stump portion 7 and closes only at higher speeds of discharge air flow when the patient breathes out. In this arrangement also a rotary movement of the valve housing 9 provides for adjustment in respect of the air speed at which the valve flap 18 closes.

In its wall which is in opposite relationship to the passage stump portion 7, the tube portion 10 has an opening 25 through which the voice prosthesis 5 leads into the closure device 6 (see FIG. 1). Instead of the opening 25 the tube portion 10 may also be completely open, as shown by the perspective view in FIG. 14.

The embodiment illustrated in FIG. 9 differs from the above-described embodiment in that the valve housing 29 is now formed or molded in one piece on the passage stump 7. In other respects the valve with its flap 18 and the magnets 21 and 22 corresponds to the embodiment shown in FIGS. 2 through 5. A corresponding point also applies in respect of the flange ring 8 and the tube portion 10.

Similarly as in the embodiment shown in FIGS. 2 through 5, the valve flap 18 with its radial extension portion 17 is fixed in the valve housing 29 by the extension portion 17 being passed through a slot 30. In that arrangement, unlike the construction shown in FIG. 6, the radial extension portion has two webs 19 acting as abutment or stop means; after the valve flap 18 with its radial extension portion 17 has been fitted into the valve housing 29, one web 19 lies outside the valve housing 29 and the other web 19 lies within the valve housing 29. As the view on an enlarged scale in FIG. 10 shows, the slot 30 is of an enlarged width in the peripheral direction in such a way that the radial extension portion 17 can be displaced in the peripheral direction in the slot 30. That makes it possible to provide the same adaptation effect as is achieved by rotary movement of the valve housing 9 in the embodiment shown in FIGS. 2 through 5. Unlike the view shown in FIG. 10, the slot 30 is of such a configuration that the edges thereof bear sealingly against each other, at the locations where the extension portion 19 is not disposed.

FIG. 12 is a side view of the valve flap 18 shown in FIG. 11. FIG. 12 shows the rest position thereof, that is to say that position in which the flap 18 was produced, with its extension portion 17. By virtue of that arrangement, it is additionally possible, by way of the hinge 20, to generate a spring force which urges the valve plate or disc 18 into the rest position shown in FIG. 12.

FIG. 13 is a further perspective view of the embodiment shown in FIG. 9. Instead of the tube portion 10 with opening 25, this arrangement may also use the tube portion 10 which is cut open in a channel-like configuration, as illustrated in FIG. 14. In the end regions 33 which are identified by dash-dotting, the tube portion 10 is advantageously produced from material which is made soft, thereby avoiding irritation or even injury to the patient.

While the embodiment shown in FIGS. 2 through 5 already provides that the structural height of the closure device and in particular that dimension with which the closure device projects from the stoma has been substantially reduced in comparison with the state of the art, the embodiment shown in FIG. 9 provides a further improvement in that direction by virtue of the integrated valve housing 29. For aesthetic reasons, such a reduction in structural height is a particularly important consideration for the patient.

What is claimed is:

1. A tracheostoma closure device comprising:
   a valve actuable at will by a patient when breathing out to permit the patient to speak,
   said valve being movable to either of a closed position or an opened position;
   said valve including means for magnetically holding said valve in said opened position until selectively moved to said closed position by said patient; said magnetically holding means further comprising a first magnet located on a valve flap and a second magnet located on a valve housing, said first and second magnets cooperating by magnetic attraction to hold said valve flap in said opened condition;
   means for adjusting said magnetic attraction between said first and second magnets, said adjusting means being adjustable by rotation of said valve flap and said valve housing with respect to one another;
   an insert means comprising a passage stump portion adapted to be introduced into a stoma and a terminal member adapted to be introduced into the trachea; and
   said valve housing adapted to be carried on said passage stump portion on an outward part thereof, said valve housing pivotally mounting therein a non-return valve flap which is adapted to open in the direction of breathing in and to close in the direction of breathing out when a predetermined dynamic pressure due to the air flow speed is exceeded.

2. A closure device as set forth in claim 1 and further including a flange ring adapted to be mounted on said passage stump portion.

3. A closure device as set forth in claim 1 wherein at least one of said valve flap and a valve seat therefor in said valve housing comprises flexible material such that said valve flap after closing is adapted to pass through said seat thereof when said predetermined dynamic pressure is exceeded.

4. A closure device as set forth in claim 1 wherein said valve flap is mounted in a region of said valve housing which is the lower region in the operative position thereof, and including a weighting means adapted to hold said valve flap in said opened condition.

5. A closure device as set forth in claim 1 and including spring means adapted to hold said valve flap in said opened condition.

6. A closure device as set forth in claim 1 including adjustment in respect of the force with which said valve flap is held in said opened condition.

7. A closure device as set forth in claim 6 wherein means for displacement of the mounting location of said valve flap in the peripheral direction of said passage stump portion are provided.

8. A closure device as set forth in claim 7 wherein said displacement means comprise means mounting said valve housing on said passage stump portion rotatably with respect thereto.

9. A closure device as set forth in claim 8 wherein said displacement means include a peripherally extending bead portion on said passage stump portion in the region of its contact surface with said valve housing.

10. A closure device as set forth in claim 9 wherein said displacement means include a peripherally extending bead portion on said valve housing in the region of its contact surface with said passage stump portion.

11. A closure device as set forth in claim 1 wherein said valve housing is part of said passage stump portion.

12. A closure device as set forth in claim 1 wherein said valve housing has a slot therethrough, wherein an extension portion extends sealingly through said slot into said valve housing, and connected to said extension portion.

13. A closure device as set forth in claim 12 wherein said pivotal connection between said disc and said extension portion comprises a film hinge.

14. A closure device as set forth in claim 12 including at least one abutment means on said extension portion to define and delimit the depth of insertion into said valve housing.

15. A closure device as set forth in claim 12 wherein said slot is of such a width in the peripheral direction of the valve housing that said extension portion with said valve flap is adjustable in its angular position with respect to said valve housing.

16. A closure device as set forth in claim 12 wherein said valve disc with its extension portion and said film hinge is produced from a resilient plastic material.

17. A closure device as set forth in claim 16 wherein said plastic material is a polyacetate resin (POM).

18. A closure device as set forth in claim 2 wherein said flange ring has a cut-away portion on a part of the periphery thereof.

19. A closure device as set forth in claim 2 wherein said flange ring has a radially projecting bar portion having a bore therein and wherein a holding means connected to said valve housing is fixed in said bore.

20. A closure device as set forth in claim 19 wherein said holding means is a thread.

21. A closure device as set forth in claim 19 wherein said holding means is a tape.

22. A closure device as set forth in claim 1 wherein said passage stump portion has a radially projecting bar portion and including a holding means connecting said valve housing to said bar portion.

23. A closure device as set forth in claim 1 wherein said terminal member is a tube portion fitted on to the inner end of said passage stump portion and open with respect thereto.

24. A closure device as set forth in claim 23 wherein said tube portion is joined to the rearward end of said passage stump portion, said tube portion possessing angled end surfaces.

25. A closure device as set forth in claim 23 wherein said tube portion has an opening at the wall thereof which is in opposite relationship to said passage stump portion opposite said passage stump portion.

26. A closure device as set forth in claim 23 wherein said tube portion is completely opened opposite said passage stump portion.

27. A closure device as set forth in claim 23 wherein said tube portion is produced from material which is made soft in the region of the ends thereof.

28. A closure device as set forth in claim 1 which is made from silicone rubber.

* * * * *